(12) United States Patent
Riach (10) Patent No.: US 7,048,703 B2
(45) Date of Patent: May 23, 2006

(54) SUPPORT DEVICE

(75) Inventor: Jeffrey M. Riach, Cockeysville, MD (US)

(73) Assignee: Oakworks, Inc., New Freedom, PA (US)

( * ) Notice: Subject to any disclaimer, the term of this patent is extended or adjusted under 35 U.S.C. 154(b) by 153 days.

(21) Appl. No.: 10/324,138

(22) Filed: Dec. 20, 2002

(65) Prior Publication Data

US 2003/0139695 A1 Jul. 24, 2003

Related U.S. Application Data

(60) Provisional application No. 60/341,829, filed on Dec. 21, 2001.

(51) Int. Cl.
*A61F 5/00* (2006.01)

(52) U.S. Cl. .......................... 602/13; 602/61; 128/845; 5/655.3

(58) Field of Classification Search ................ 601/148, 601/149, 150, 151; 602/6, 13, 26, 60, 61–63; 128/DIG. 20, 845, 846, 847, 856; 5/652, 5/654, 655.3, 710, 713
See application file for complete search history.

(56) References Cited

U.S. PATENT DOCUMENTS

| | | | | |
|---|---|---|---|---|
| 2,728,926 A | * | 1/1956 | Emery | 5/655.3 |
| 4,986,260 A | * | 1/1991 | Iams et al. | 601/43 |
| 5,588,956 A | * | 12/1996 | Billotti | 602/13 |
| 5,626,557 A | * | 5/1997 | Mann | 602/26 |
| 5,785,669 A | * | 7/1998 | Proctor et al. | 601/148 |
| 5,954,676 A | * | 9/1999 | Kramer, III | 602/6 |
| 5,997,495 A | * | 12/1999 | Cook et al. | 602/62 |
| 6,402,712 B1 | * | 6/2002 | Gauvry | 602/26 |
| 6,488,643 B1 | * | 12/2002 | Tumey et al. | 602/13 |
| 6,546,579 B1 | * | 4/2003 | Leventhal et al. | 5/655.3 |
| 6,592,534 B1 | * | 7/2003 | Rutt et al. | 601/151 |

\* cited by examiner

*Primary Examiner*—Quang D. Thanh
(74) *Attorney, Agent, or Firm*—Nixon Peabody LLP; Daniel S. Song (57) ABSTRACT

A support device for providing enhanced support to users. In one embodiment, the support device includes a first bladder and a second bladder. Valves may be attached to the bladders to allow inflation and/or deflation of the bladders. In yet another embodiment, the support device is further provided with a pump attached to the bleed valve. In one embodiment, the support device is provided with bladders having a kidney bean shape and the support device has a butterfly shape. In another embodiment, the support device may be implemented with four wing portions configured to define four recesses, each of the recesses being positioned between two adjacent wing portions so that the support device has a shape of a butterfly. In this regard, the support device may include an air bladder, or be made of foam.

18 Claims, 4 Drawing Sheets

SUPPORT DEVICE

This application claims priority to U.S. Provisional Application No. 60/341,829, filed Dec. 21, 2001.

BACKGROUND OF THE INVENTION

1. Field of the Invention

The present invention is directed to a support devices for elevating and/or supporting different areas of the user's body.

2. Description of Related Art

In various medical, rehabilitation, and massage therapy fields, patients or other individuals must often be positioned in a particular posture so that appropriate treatment, such as massage services, can be readily provided. In this regard, various support devices have been created to provide the required support to such individuals. Presently, support devices are generally made of foam or some other resilient material, or are alternatively made of an inflatable bladder.

Conventional foam support devices only offer a single degree of height support for the patient or individual. In addition, although foam support devices that support the chest area of an individual are known, these support devices may or may not fit the individual's anatomy. Because they are fixed in height and typically are relatively thick, additional support devices are needed to provide full support of the individual utilizing such conventional foam support devices. Their size and weight also reduce the portability and utility of conventional foam support devices.

Conventional inflatable support devices on the other hand, allow the height of the support device to be adjusted. This may be attained by adjusting the amount of air used to inflate the support device. However, despite the advantages provided by the conventional inflatable support devices, these support devices are limited in their adjustability. In addition, due to their shape, conventional support devices have limited utility. Conventional support device do not offer desirable support of the chest area for patients or individuals.

SUMMARY OF THE INVENTION

In view of the foregoing, there still exists an unfulfilled need for support devices that allow additional adjustability than that possible with conventional support devices. In addition, there also exists an unfulfilled need for support devices that provide comfortable support of different areas of the user's body, including the chest area.

In the above regard, an advantage of one embodiment of the present invention is in providing highly adjustable support devices for supporting different areas of the body in a way which offers more adjustability, comfort, and increased stability.

Another advantage of another embodiment of the present invention is in providing support devices that are light weight and can be made compact for portability.

Still another advantage of another embodiment of the present invention is in providing a support device for relieving the pressure on chest of individuals when they are in a prone position.

Yet another advantage of the present invention is in providing such support devices that are economical and durable.

These and other advantages are attained by an support device in accordance with one embodiment including a first bladder with a bladder opening adapted to allow inflation and deflation of the first bladder, and a second bladder with a bladder opening adapted to allow inflation and deflation of the second bladder. In one embodiment, the first bladder and the second bladder are conjoined together by a sealing divider.

In another embodiment of the present invention, the support device also includes a protective cover that encapsulates the first bladder and the second bladder. The protective cover may include at least one opening to allow access to the first bladder and/or the second bladder. In this regard, the opening may be closable via a zipper, velcro, buttons, or snaps. The provision of a protective cover allows the first bladder to be separate from the second bladder in another embodiment of the support device of the present invention. The protective cover may be made of vinyl, fabric, leather, or rubber.

In accordance with one embodiment, the support device further includes a valve attached to each bladder opening, the valve being adapted to control inflation and/or deflation of the bladder. In another embodiment, the support device includes a hose attached to the bladder opening of the first bladder, and a bleed valve attached to the hose, the bleed valve being operable to control inflation and/or deflation of the first bladder. In yet another embodiment, the support device is further provided with a pump attached to the bleed valve, for example, a bulbous manual pump with an integral one way valve.

In accordance with still another embodiment, the support device is substantially cylindrical in shape whereas in another embodiment, the support device has a shape of a butterfly. In such an embodiment, the first bladder and the second bladder are shaped to loosely resemble kidney beans and have wing portions that define recesses. Any appropriate materials may be used for the first bladder and the second bladder such as vinyl, polypropylene, and rubber.

In accordance with another embodiment of the present invention, the above advantages and others are provided by an support device including a first bladder having a kidney bean shape with a bladder opening adapted to allow inflation and deflation of the first bladder, and a second bladder having a kidney bean shape with a bladder opening adapted to allow inflation and deflation of the second bladder.

In one embodiment, the first bladder and the second bladder are connected together by a sealing divider in a manner that the support device has a butterfly shape. In another embodiment, the support device further includes a protective cover adapted to encapsulate the first bladder and the second bladder therein, the protective cover having a butterfly shape.

In yet another embodiment, the support device further includes hoses attached to the bladder openings, and bleed valves attached to the hoses, the bleed valves being operable to control inflation and deflation of the first bladder and the second bladder. Pumps may be provided which are attached to the bleed valves. In this regard, the pump may be a bulbous manual pump having an integral one way valve.

In still another embodiment of the present invention, the support device may be implemented with four wing portions configured to define four recesses, each of the recesses being positioned between two adjacent wing portions so that the support device has a shape of a butterfly.

In one implementation, the support device includes at least one bladder with a bladder opening adapted to allow inflation and deflation of the bladder. In this regard, a hose may be attached to the bladder opening, and bleed valve attached to the hose, the bleed valve being operable to control inflation and deflation of the bladder. Moreover, a bulbous manual pump may be attached to the bleed valve for allowing inflation of the bladder, the pump having an integral one way valve.

Preferably, the support device is compressible to provide comfortable support to the user. In this regard, the support device may be made of foam or alternatively, include a sealed bladder.

These and other advantages and features of the present invention will become more apparent from the following detailed description of the preferred embodiments of the present invention when viewed in conjunction with the accompanying drawings.

DETAILED DESCRIPTION OF THE PREFERRED EMBODIMENT

Figure 1A:
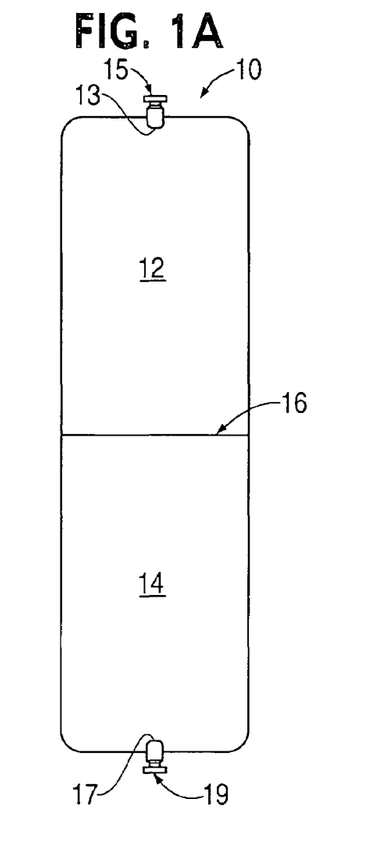
FIG. 1A is a top view of a support device in accordance with one embodiment of the present invention.
Figure 1B:
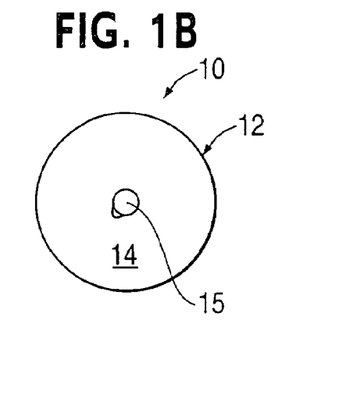
FIG. 1B is an end view of the support device of FIG. 1A.

FIGS. 1A and 1B each show one embodiment of the support device 10 in accordance with the present invention which allows improved adjustability and provides additional functionality as described herein below. It should initially be noted that in the illustrated embodiment, the support device 10 is cylindrically shaped as most clearly shown in FIG. 1B. However, other support devices having different shapes may also be practiced in accordance with the present invention. Thus, a support device having a triangular shape, rectangle shape, or other shape may be provided with plurality of bladders of the present invention.

The support device 10 as shown in FIGS. 1A and 1B is of the inflatable type made from an air tight material such as rubber, vinyl, polypropylene or any other appropriate material. In contrast with the prior art support devices, the support device 10 is provided with a plurality of bladders in the present embodiment, a first bladder 12, and a second bladder 14. In the illustrated embodiment, the first and second bladders 12 and 14 respectively, are conjoined together by a sealing divider 16. The first bladder 12 may be inflated and deflated using valve 15 which is attached to bladder opening 13. Likewise, the second bladder 14 may be inflated or deflated using valve 19 attached to bladder opening 17. Thus, it should be apparent that the first bladder 12 may be inflated and deflated wholly independent of the second bladder 14, and vice versa. Of course, it should be noted that whereas the illustrated embodiments are provided with two bladders, other embodiments of the present invention may be implemented having more than two bladders, for example, three or four bladders.

The valves 15 and 19 may be implemented using conventional inflation nozzles having a valve mechanism such as those used in inflatable toys and flotation devices. Such valve mechanisms allow the user to blow into the bladders without the air being released from the bladders. However, by squeezing the sides of the valve mechanism, air is released through the valve mechanism. Of course, other types of valves may be used instead in other embodiments.

By providing the first bladder 12 and the second bladder 14, the support device 10 may be advantageously used to provide better support than was possible using prior art support devices. In particular, in the illustrated embodiment of FIGS. 1A and 1B, the support device 10 may be used to support the knees of an individual receiving treatment, one knee resting on the first bladder 12 while the other knee rests on the second bladder 14.

In an application where massage services are provided to the individual, the separately inflatable bladders 12 and 14 prevent movement of air from one bladder to the other within the support device 10. Thus, if the massage professional exerts pressure on the knee supported by the first bladder 12, the other knee supported on the second bladder 14 would remain substantially still with minimal upward movement. Again, this is made possible due to the fact that the first bladder 12 is separately inflatable relative to the second bladder 14. Therefore, the present invention minimizes unwanted movement of an individual when pressures change from one section of the device to another. Of course, the support device 10 may be used in other applications as well, such as household use for providing support and application to massage services as described herein is merely one example.

In addition, by providing a plurality of bladders, the present invention also minimizes rolling of the individual since the rolling movement is resisted by the adjacent air bladder. For example, in the massage services application, this stabilization of the individual's body helps to increase relaxation and increases the massage therapist's control of the position of the individual's body. Moreover, it should be noted that the support device 10 may be utilized in other support applications as well, such as under the pelvis in a prone positioning of the individual to raise the individual's diaphragm off the surface and facilitate easier breathing. Again, the stability provided by the plurality of bladders resists rolling motion of the individual to thereby facilitate treatment in such applications.

The plurality of bladders, in this example, the first bladder 12 and the second bladder 14 of the support device 10 in accordance with the present invention can be inflated in unison to thereby allow lowering or raising the level of support provided by each of the bladders. The bladders can also be differentially inflated to accommodate asymmetrical positioning requirements that may be desired or required to effectively treat the individual. For instance, the first bladder 12 may be inflated to a higher position than the second bladder 14 so that one knee of the individual is elevated higher than the second knee. Thus, the support device in accordance with the present invention provides adjustable support while also providing stability of positioning, and the ability to create asymmetrical positioning by inflating one bladder more than the other. Moreover, as can readily be appreciated, the support device 10 can be deflated to facilitate transportability.

Figure 2:
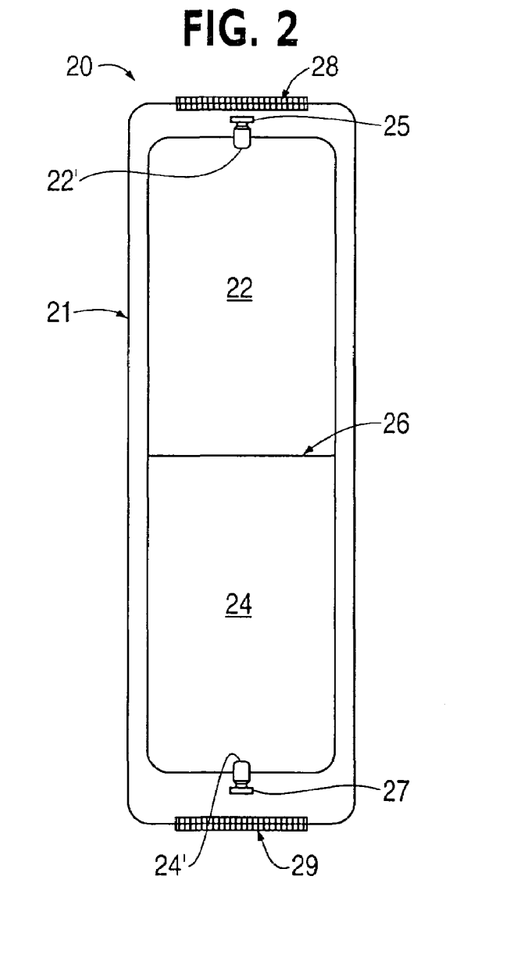
FIG. 2 is a schematic illustration of a support device in accordance with another embodiment of the present invention including a protective cover.

FIG. 2 illustrates a support device 20 in accordance with another embodiment of the present invention which includes a protective cover 21 that houses the first bladder 22 and the second bladder 24. Like the embodiment of FIGS. 1A and 1B, the first and second bladders 22 and 24 are separated by a sealing divider 26. In addition, the first bladder 22 includes valve 25 attached to bladder opening 22', and the second bladder 24 includes valve 27 attached to bladder opening 24'. The valves 25 and 27 allow inflation and/or deflation of the first and second bladders 22 and 24, respectively.

The cover 21 is preferably made of flexible, and yet durable material such as vinyl, leather, fabric, rubber, or other appropriate material so as to protect the support device 20 and resist against puncture or tearing of the first bladder 22 and the second bladder 24. Such protection is desirable since any puncture or tear of the support device 20 will cause the first bladder 22 and/or the second bladder 24 to deflate.

To allow access to the valves 25 and 27, the cover 21 may be provided with openings 28 and 29 which are positioned proximate to the valves 25 and 27, respectively, to allow access thereto. In one embodiment, the openings may be provided with a zipper as shown to allow closure of the openings. Of course, different types of closures can also be used as well such as velcro, buttons, snaps, etc.

Moreover, in such an embodiment where a cover is provided, two separate bladders may be used instead of the first and second bladders conjoined by a sealing divider as shown in FIGS. 1A and 2. Such an embodiment is show in FIG. 3 that illustrates a support device 30 having a first bladder 32 which is separate from a second bladder 34, both of which are provided in the protective cover 36. In the manner previously described, the first bladder 32 may be inflated/deflated using the valve 33 attached to the bladder opening 32' and the second bladder 34 may be inflated/deflated using the valve 35 attached to the bladder opening 34'. The protective cover 36 may be provided with openings 37 and 38 proximate to valves 33 and 35, respectively, to provide access thereto.

Figure 3:
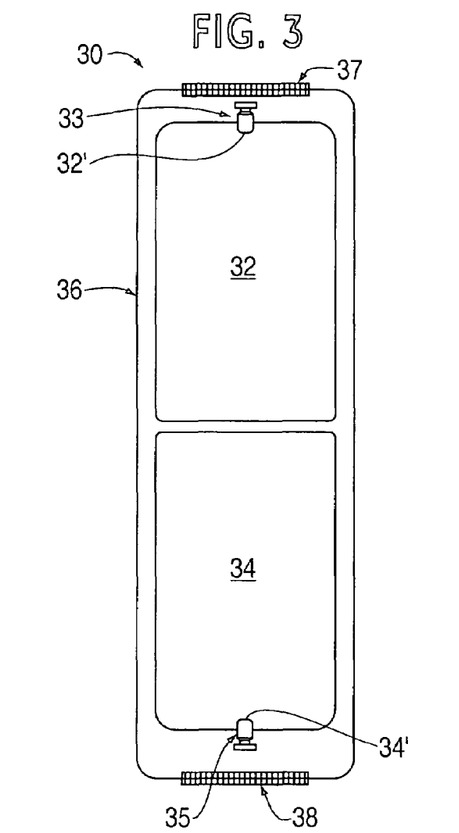
FIG. 3 is a schematic illustration of a support device in accordance with still another embodiment of the present invention.

This embodiment of the support device 30 as shown in FIG. 3 is especially advantageous in facilitating manufacturing of the support device since the first bladder 32 and the second bladder 34 would be the same, and a sealing divider is not required. Moreover, providing two separate bladders allows one of the bladders to be replaced in the event that it is damaged while the other bladder reused, instead of requiring the replacement of both bladders. For example, if the first bladder 32 is punctured, it may be removed and replaced while the second bladder 34 is reused thereby minimizing repair costs.

Figure 4:
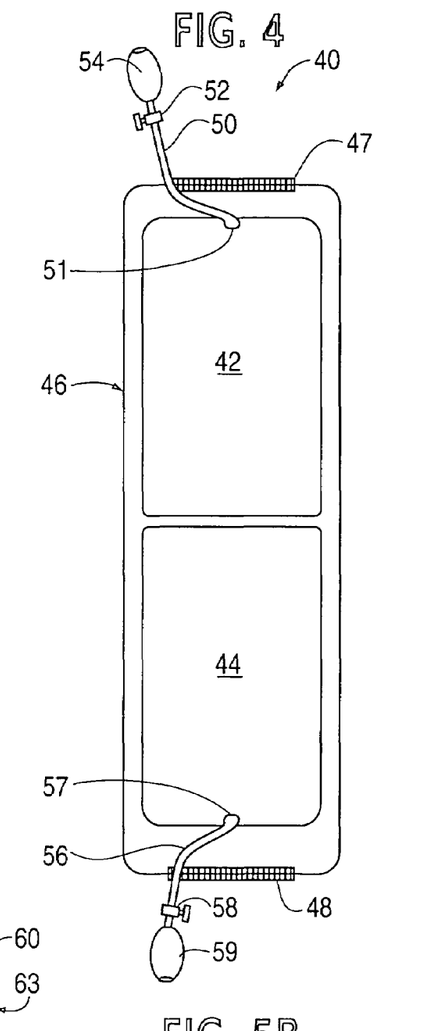
FIG. 4 is a schematic illustration of a support device in accordance with yet another embodiment of the present invention having pumps integrated thereto.

FIG. 4 is a schematic illustration of a support device 40 in accordance with yet another embodiment of the present invention. The support device 40 has a first bladder 42 which is separate from a second bladder 44, both of which are provided in the protective cover 46. The protective cover 46 is provided with openings 47 and 48 to provide access to the bladders. In the illustrated embodiment, the first bladder 42 is provided with a hose 50 that is attached to bladder opening 51 at one end, and is attached to a bleed valve 52 at the other end, the bleed valve 52 being operable to allow inflation and/or deflation of the bladder 42. The bleed valve 52 is attached to a pump 54 that is operable to inflate the first bladder 42. In this regard, the pump 54 of the illustrated embodiment is a bulbous hand pump with a one way check valve, such pumps being commonly used in medical applications to check blood pressure in patients. Of course, other types of pumps may be used in other embodiments of the present invention and pump 54 is merely provided as one example. By having the bleed valve 52 in an appropriate position and by repeatedly squeezing the pump 54, the bladder 42 may be inflated a desired amount. Moreover, the bleed valve 52 may further be operated to deflate the first bladder 42.

In a like manner, the second bladder 44 is provided with a hose 56 that is attached to bladder opening 57 at one end, and is attached to a bleed valve 58 at the other end. The bleed valve 58 is attached to a pump 59 and may be used in the manner previously described to inflate and/or deflate the second bladder 44. By providing such integral valves and pumps, the support device 30 may be easily inflated and/or deflated as desired to provide appropriate level of support. In addition, the amount of support provided may be adjusted while an individual is being supported on the support device 40. Moreover, by providing separate valves and pumps, each of the bladders may be inflated and/or deflated independently of one another thereby allowing different levels of support.

Figure 5A:
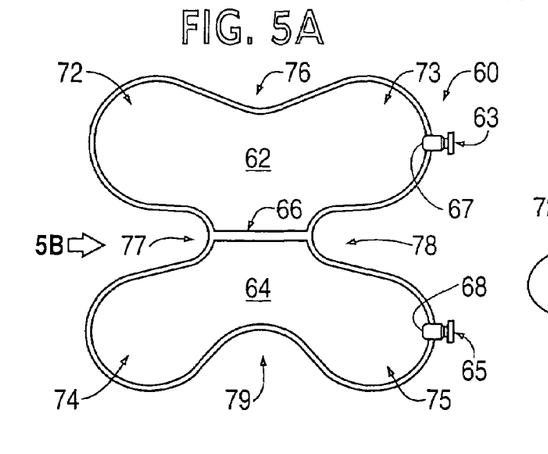
FIG. 5A is a top view of a support device in accordance with another embodiment of the present invention.
Figure 5B:
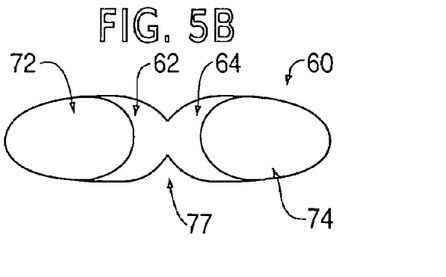
FIG. 5B is an end view of the support device of FIG. 5A.

FIGS. 5A and 5B show a support device 60 in accordance with another embodiment of the present invention. The support device 60 is also provided with a first bladder 62 and a second bladder 64 which are conjoined by the sealing divider 66. Valve 63 is attached to the bladder opening 67 to allow inflation and deflation of the first bladder 62, and valve 65 is attached to bladder opening 64 to allow inflation and deflation of the second bladder 64. As will be described in further detail herein below, the support device 60 in accordance with the illustrated embodiment is uniquely shaped to provide numerous different support functions. In addition, the unique shape provides especially comfortable and adjustable support of the individual's chest and is particularly suited to provide chest support for women.

As can be seen by the examination of FIG. 5A, the support device 60 is uniquely shaped with various curvatures so that the support device 60 loosely resembles a butterfly or a "four leaf" clover. In this regard, the first bladder 62 of the support device 60 has a shape loosely resembling a kidney bean and includes wing portions 72 and 73. Likewise, the second bladder 64 also has a shape loosely resembling a kidney bean and includes wing portions 74 and 75, as shown. The first bladder 62 and the second bladder are conjoined by the sealing divider 66 in the present embodiment. The wing portions of the bladders form various recessed regions. In particular, the support device 60 is provided with an upper recessed region 76, side recessed regions 77 and 78, and a lower recessed region 79. These recessed regions of the support device 60 provides enhanced comfort to the user as well as providing additional functionality as described below.

For example, the unique shape of the support device 60 in the illustrated embodiment relieves the pressure off the breasts of the individual when the individual is in a prone position lying on the support device 60, and also allows easy breathing by the individual. This relief of pressure off the breasts and facilitation of breathing is attained by the unique shape of the support device 60 which supports primarily the bony structures of the individual. In this regard, when the support device 60 is used to support an individual in a prone position, the upper recess 76 of the support device 60 defines a neck recess so that the individual's breathing is not impeded by the first air bladder 62 when the individual's shoulders are supported by the wing portions 72 and 73 of the first bladder 62. In addition, the lower recess 79 defines an abdominal recess that further facilitates the individual's breathing even when the individual's mid-section is supported by the wing portions 74 and 75 of the second bladder 64.

Because the first bladder 62 and the second bladder 64 are separately inflatable using the valves 63 and 65, respectively, the amount of support provided by the first bladder 62 may be adjusted as needed relative to the second bladder 64 and vise-versa, depending on the anatomy of the individual being supported by the support device 60. For instance, to facilitate the individual's breathing, the second bladder 64 may be underinflated relative to the first bladder 62.

In addition to the above functionality, the support device 60 is further uniquely shaped to relieve the pressure on the breasts of women when they are in a prone position being supported by the support device 60. In this regard, the side recesses 77 and 78 define breast recesses that can receive at least a portion of a woman's breasts while being supported by the support device 60. Because of the amount of support and height elevation provided by the support device 60 is readily adjustable by the amount of inflation of the first bladder 62 and the second bladder 64, the support device 60 can readily be adjusted to accommodate individuals having breasts of various sizes. As compared to the prior art support devices, the support device 60 in accordance with the present invention is thin, height adjustable, and offers superior comfort and support, especially to women. Hence, as described, it should be clear how the support device 60 in accordance with the illustrated embodiment may be adjusted to accommodate the wide variety of anatomies.

Furthermore, the unique butterfly shape of the support device 60 of FIG. 5A also provides increased functionality in addition to that described above. For example, the support device 60 may be used as a lumbar support by partially folding the support device 60 along the sealing divider 66 so that the second bladder 64 is stacked above the first bladder 62. In this configuration, the upper recess 76 and the lower recess 79 are aligned to define a lumbar recess for receiving and supporting the user's back, the wings 72, 73, 74, and 75 providing lumbar support to the individual. In such a configuration, the support device 60 may also be used as a pelvic tilting device for angling the pelvis, or as a cervical pillow for supporting the individual's neck when the user is laying on his/her back.

Figure 6:
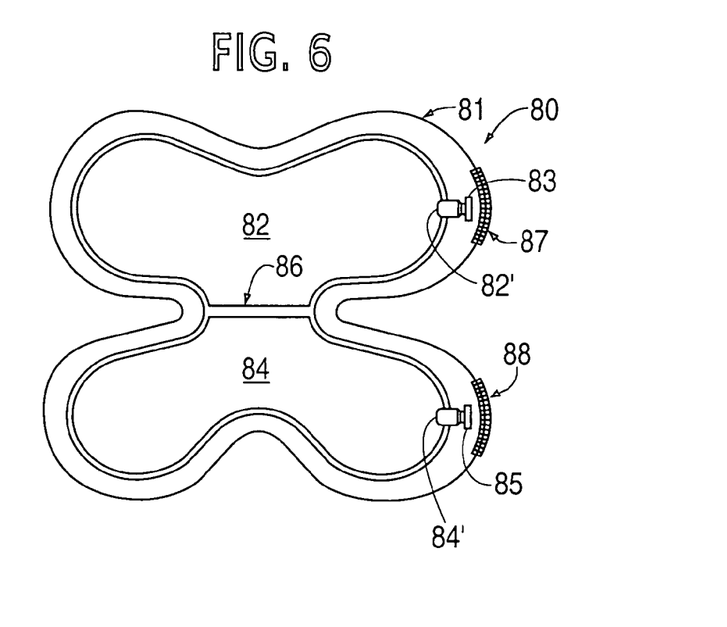
FIG. 6 is a schematic illustration of the support device in accordance with still another embodiment of the present invention including a protective cover.

FIG. 6 is a schematic illustration of the support device 80 in accordance with still another embodiment of the present invention which includes a protective cover 81 that resists damage to the first bladder 82 and the second bladder 84. As shown, each bladder has a kidney bean shape and the first bladder 82 is conjoined to the second bladder 84 via a sealing divider 86. The conjoined bladders together have a shape resembling a butterfly or a four leaf clover. In addition, the cover 81 of the support device 80 is correspondingly shaped to resemble a butterfly or a four leaf clover to allow encapsulation and protection of the first and second bladders 82 and 84. This unique shape of the support device 80 provides the various functionality and manners of use previously described relative to the support device 60 of FIGS. 5A and 5B.

The first bladder 82 may be inflated/deflated using the valve 83 attached to the bladder opening 82' and the second bladder 84 may be inflated/deflated using the valve 85 attached to the bladder opening 84'. In a manner similar to the embodiment shown in FIG. 2, the cover 81 is provided with openings 87 and 88 that provide access to the valves 83 and 85. Of course, the first bladder 82 and the second bladder 84 may be inflated and/or deflated independently relative to one another. In the illustrated example, the openings 87 and 88 are also provided with zippers to allow the openings to be closed. Of course, different types of closures can also be used as well such as velcro, buttons, snaps, etc. as also previously noted.

Figure 7:
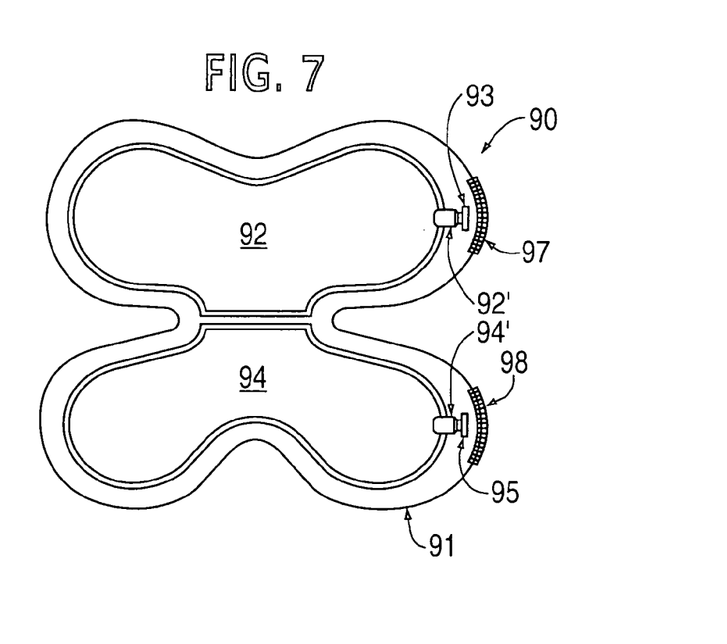
FIG. 7 is a schematic illustration of a support device in accordance with still another embodiment of the present invention.

Moreover, it should also be noted that if the support device is provided with such a protective cover, the first bladder may be separate from the second bladder rather than being enjoined together by a sealing divider. In this regard, FIG. 7 shows a support device 90 in accordance with yet another embodiment of the present invention. As can be seen, the kidney bean shaped first bladder 92 is separate from the kidney bean shaped second bladder 94, both of which are provided within the protective cover 91. The first bladder 92 may be inflated/deflated using the valve 93 attached to the bladder opening 92' and the second bladder 94 may be inflated/deflated using the valve 95 attached to the bladder opening 94'. The protective cover 91 also includes openings 97 and 98 that allow access to the valves 93 and 95, respectively. Of course, whereas in the illustrated example, the openings 97 and 98 are also provided with zippers, different types of closures can also be used.

Figure 8:
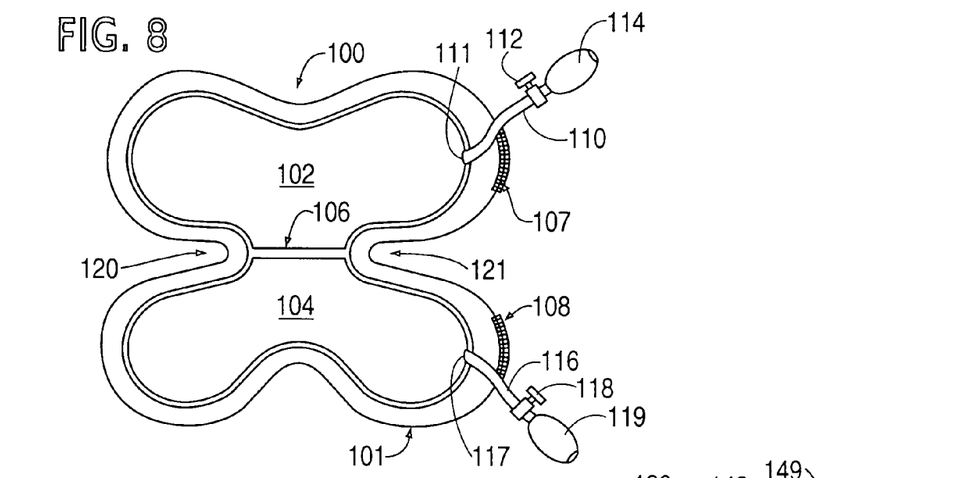
FIG. 8 is a schematic illustration of a support device in accordance with still another embodiment of the present invention having pumps integrated thereto.

FIG. 8 is a schematic illustration of a support device 100 in accordance with still another embodiment of the present invention that has a shape resembling a butterfly or a four leaf clover. As shown, the support device 100 includes a protective cover 101 shaped in a corresponding manner that resists damage to the kidney bean shaped first bladder 102 and the second bladder 104. In the present embodiment, the first bladder 102 is conjoined to the second bladder 104 via the sealing divider 106. The protective cover 101 is provided with openings 107 and 108 to provide access to the bladders.

Like the embodiment of FIG. 3 discussed previously, the first bladder 102 is provided with a hose 110 that is attached to bladder opening 111 at one end, and is attached to a bleed valve 112 at the other end, the bleed valve 112 being operable to allow inflation and/or deflation of the bladder 102. The bleed valve 112 is attached to a pump 114 that is operable to inflate the first bladder 102. As previously discussed, the pump 114 may be a bulbous hand pump with a one way check valve as used in medical applications, or other types of pumps. By having the bleed valve 112 in an appropriate position and by squeezing the pump 114, the bladder 102 may be inflated a desired amount. Moreover, the bleed valve 102 may further be operated to deflate the first bladder 102.

In a like manner, the second bladder 104 is provided with a hose 116 that is attached to bladder opening 117 at one end, and is attached to a bleed valve 118 at the other end. The bleed valve 118 is attached to a pump 119 and may be used to inflate and/or deflate the second bladder 104. By providing such integral valves and pumps, the support device 100 may be easily inflated and/or deflated independently as desired to provide appropriate level of support. Moreover, the amount of support provided may be adjusted while an individual is being supported on the support device 100.

In the above regard, the support device 100 may be used as a cervical traction device with left and right side adjustability. This may be attained by partially folding the support device 100 perpendicular to the sealing divider 106 so that the first and second bladders 102 and 104 are essentially folded in half. In this configuration, the side recesses 120 and 121 align above one another to define a neck recess for receiving and supporting the individual's neck. By inflating the first bladder 102 and/or the second bladder 104, the neck can be gently stretched. In addition, the independent inflatability of the first bladder 102 and the second bladder 104 allows increased traction on one side of the neck more than the other. This provides more flexibility in use as compared to conventional cervical traction devices that are available to consumers.

The inflatable features of the present embodiments discussed above are especially advantageous because height of the bladders can be readily adjusted, the support device is very lighter in weight, and very portable since it can be deflated and collapsed. It should further be noted that whereas in the various embodiments shown and described above, only two bladders are provided for each of the support devices, in other embodiments, additional bladders may also be provided such as three bladders or even four bladders.

In view of the above, it should be evident how the present invention provides a unique support device with a plurality of bladders that may be independently adjusted to provide superior comfort and support to individuals using a support device. It should also be evident how the present invention provides additional functionality as compared to the prior art support devices. It should especially be evident how the support device may be used to support the chest of individuals and to increase comfort, especially for women. Of course, alternative embodiments of the present invention may be implemented as described below without some of the various features described above.

Figure 9:
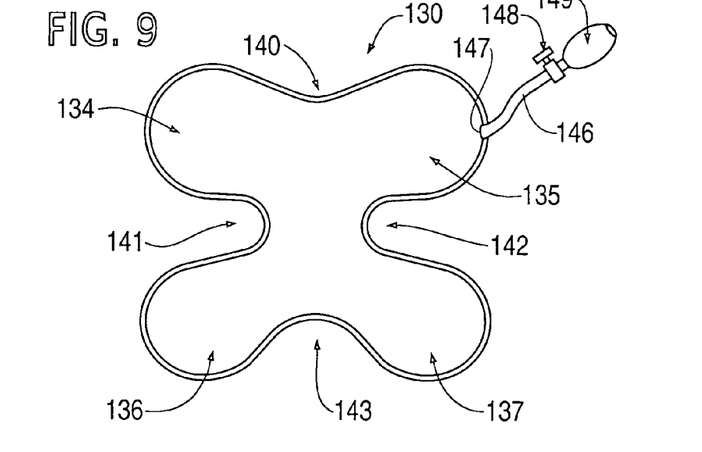
FIG. 9 is a schematic illustration of a support device in accordance with yet another embodiment of the present invention.

For example, FIG. 9 is a schematic illustration of a support device 130 in accordance with yet another embodiment of the present invention. The support device 130 is provided with four wing portions 134, 135, 136 and 137 that are configured to define four recesses 140, 141, 142, and 143, each of the recesses being positioned between two adjacent wing portions. Thus, like the embodiments of FIGS. 5A to 8 described above, the support device 130 has a shape of a butterfly.

In addition, as shown in FIG. 9, the support device 130 includes an inflatable bladder 132 that can be inflated and/or deflated to provide desired level of support. However, in contrast to the embodiments of FIGS. 5A to 8 in which a plurality of bladders were provided, the illustrated support device 130 of FIG. 9 is provided with just one bladder 132. Of course, in other embodiments, the support device may be further provided with a protective cover that encapsulates the bladder 132 in the manner previously described to resist tearing or other damage to the bladder 132.

The support device 130 is provided with a hose 146 that is attached to bladder opening 147 at one end, and is attached to a bleed valve 148 at the other end, the bleed valve 148 being operable to allow inflation and/or deflation of the bladder 132. The bleed valve 148 is attached to a pump 149 that is operable to inflate the bladder 132. As previously discussed, the pump 149 may be a bulbous hand pump with a one way check valve as used in medical applications, or other types of pumps. By having the bleed valve 112 in an appropriate position and by squeezing the pump 114, the bladder 134 may be inflated a desired amount. Moreover, the bleed valve 148 may further be operated to deflate the bladder 134.

Because the support device 130 is provided with an inflatable bladder 134 and is configured to have a butterfly shape with the recesses as noted, the support device 130 may be used to provide adjustable chest support, lumbar support, or as a traction device as previously described. However, because only one bladder 134 is provided, the support device 130 is not as adjustable as the embodiments of FIGS. 5A to 8 which utilize a plurality of inflatable bladders.

Figure 10:
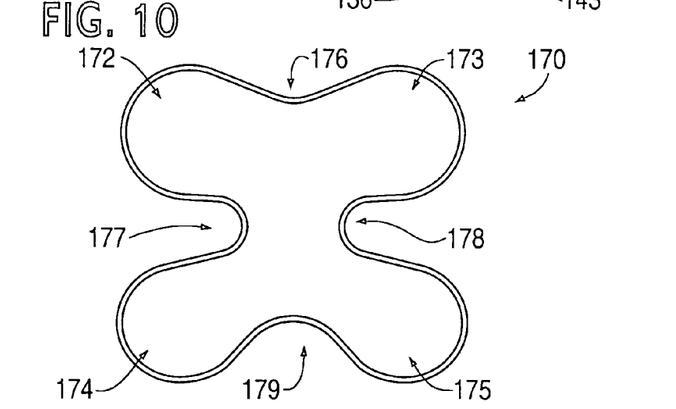
FIG. 10 is a schematic illustration of a support device in accordance with still another embodiment of the present invention.

FIG. 10 is a schematic illustration of a support device 170 in accordance with still another embodiment of the present invention. As shown, the support device 170 is provided with four wing portions 172, 173, 174 and 175 that are configured to define four recesses 176 177, 178, and 179, each of the recesses being positioned between two adjacent wing portions. Thus, like the embodiments of FIGS. 5A to 8 described above, the support device 130 has a shape of a butterfly. However, the amount of support provided by the support device 170 is not adjustable. In this regard, the support device 130 may be implemented as a single sealed bladder with air therein. Of course, a protective cover may be provided to resist tearing or other damage to the sealed bladder. Alternatively, the support device 130 may be made of compressible foam material, such materials being known in the art.

Because the support device 170 has a shape of a butterfly, it can be readily used as a chest support to provide more comfortable support to individuals than was possible with conventional support devices, especially for women. However, because the amount of support provided by the support device 170 cannot be readily adjusted, the embodiment of the support device 170 is not as conducive to alternative applications. For example, the support device 170 cannot as easily be used as a traction device as described above relative to the embodiments of FIGS. 5A to 9.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

I claim:

1. A support device comprising:
   a first bladder having a kidney bean shape with a wing portion at each distal end thereof, a recessed region between the wing portions, and a bladder opening adapted to allow inflation and deflation of said first bladder; and
   a second bladder having a kidney bean shape with a wing portion at each distal end thereof, a recessed region between the wing portions, and a bladder opening adapted to allow inflation and deflation of said second bladder, said second bladder being connected to said first bladder by a sealing divider to further define side recessed regions between wing portions of said first bladder and wing portions of said second bladder so that said support device has a four leaf clover shape.

2. The support device of claim 1, further comprising a protective cover that encapsulates said first bladder and said second bladder.

3. The support device of claim 2, wherein said protective cover includes at least one opening to allow access to at least one of said first bladder and said second bladder.

4. The support device of claim 3, wherein said at least one opening is closable via at least one of a zipper, hook and loop fastener, buttons, and snaps.

5. The support device of claim 2, wherein said protective cover is made of at least one of vinyl, leather, fabric, and rubber.

6. The support device of claim 1, further comprising a valve attached to each bladder opening, each valve being adapted to control at least one of inflation and deflation, so that said at least one of inflation and deflation for each bladder is attained independent of the other bladder.

7. The support device of claim 1, further comprising a hose attached to said bladder opening of said first bladder, and a bleed valve attached to said hose, said bleed valve being operable to control at least one of inflation and deflation of said first bladder.

8. The support device of claim 7, further comprising a pump attached to said bleed valve.

9. The support device of claim 8, wherein said pump is a bulbous manual pump.

10. The support device of claim 9, wherein said pump includes an integral one way valve.

11. The support device of claim 1, wherein said first bladder and said second bladder is made of at least one of vinyl, polypropylene, and rubber.

12. The support device of claim 1, further comprising a first pump connected to said bladder opening of said first bladder to allow inflation of said first bladder independent of said second bladder; and
a second pump connected to said bladder opening of said second bladder to allow inflation of said second bladder so that inflation of said first bladder and said second bladder are independently inflatable.

13. A support device comprising:
a first bladder having a kidney bean shape with a wing portion at each distal end thereof, a recessed region between the wing portions, and a bladder opening adapted to allow inflation and deflation of said first bladder; and
a second bladder having a kidney bean shape with a wing portion at each distal end thereof, a recessed region between the wing portions, and a bladder opening adapted to allow inflation and deflation of said second bladder;
wherein said first and second bladders are independently inflatable, and substantially define an outer peripheral shape of said support device with side recessed regions between the wing portions of said first bladder and the wing portions of said second bladder.

14. The support device of claim 13, wherein said first bladder and said second bladder are connected together by a sealing divider in a manner that said support device has a four-leaf clover shape.

15. The support device of claim 13, further comprising a protective cover adapted to encapsulate said first bladder and said second bladder therein, said protective cover having a four-leaf clover shape.

16. The support device of claim 13, further comprising hoses attached to said bladder openings, and bleed valves attached to said hoses, said bleed valves being operable to control inflation and deflation of said first bladder and said second bladder.

17. The support device of claim 16, further comprising pumps attached to said bleed valves.

18. The support device of claim 17, wherein said pump is a bulbous manual pump having an integral one way valve.

* * * * *